(12) United States Patent
Park et al.

(10) Patent No.: US 7,462,739 B2
(45) Date of Patent: Dec. 9, 2008

(54) CERAMIDE DERIVATIVES, METHOD FOR PREPARING THE SAME, AND THERAPEUTIC AGENT FOR TREATING ATOPIC DERMATITIS COMPRISING THE CERAMIDE DERIVATIVES

(75) Inventors: Byeong-Deog Park, Cheongju (KR); Jong-Kyung Youm, Dajeon (KR); Hyung-Sub Gwak, Dajeon (KR); Mi-Jung Kwon, Dajeon (KR); Hwan-Mook Kim, Dajeon (KR); Jong-Soon Kang, Cheongwon (KR); Sang-Bae Han, Cheongju (KR)

(73) Assignee: Neopharm Co., Ltd. (KR)

( * ) Notice: Subject to any disclaimer, the term of this patent is extended or adjusted under 35 U.S.C. 154(b) by 0 days.

(21) Appl. No.: 12/005,226

(22) Filed: Dec. 26, 2007

(65) Prior Publication Data

US 2008/0161272 A1   Jul. 3, 2008

(30) Foreign Application Priority Data

Dec. 27, 2006   (KR) .................. 10-2006-0134430

(51) Int. Cl.
*C07F 9/22* (2006.01)
*C07F 9/28* (2006.01)
(52) U.S. Cl. ............................ 564/15; 562/8
(58) Field of Classification Search ........... 564/15; 562/8
See application file for complete search history.

(56) References Cited

U.S. PATENT DOCUMENTS

2007/0112176 A1 * 5/2007 Seiki et al. .................. 530/350

* cited by examiner

Primary Examiner—Daniel M Sullivan
Assistant Examiner—Jennifer Y Cho
(74) Attorney, Agent, or Firm—Galgano & Associates, PLLC

(57) ABSTRACT

Disclosed are ceramide derivatives represented by the following formula 1 or 2, a method for preparing the same, and a therapeutic agent for treating atopic dermatitis including the ceramide derivatives as active ingredients:

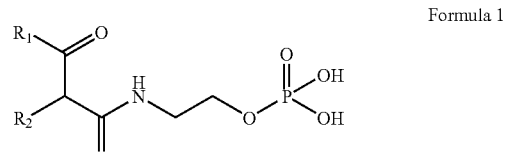

Formula 1

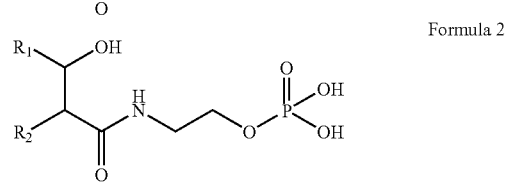

Formula 2 wherein, $R_1$ and $R_2$ are each independently straight or branched alkyl groups having 4 to 22 carbon atoms. The therapeutic agent for treating atopic dermatitis including the ceramide derivatives as active ingredients according to the present invention may be useful to treat atopic dermatitis, or treat other skin diseases that are required for improving skin inflammations or suppressing epidermal proliferation, by suppressing or improving inflammatory conditions in the atopic dermatitis in addition to giving immunoregulatory functions, and suppressing or improving skin disorders, for example epidermal proliferation that is generally observed in the atopic dermatitis.

5 Claims, 2 Drawing Sheets

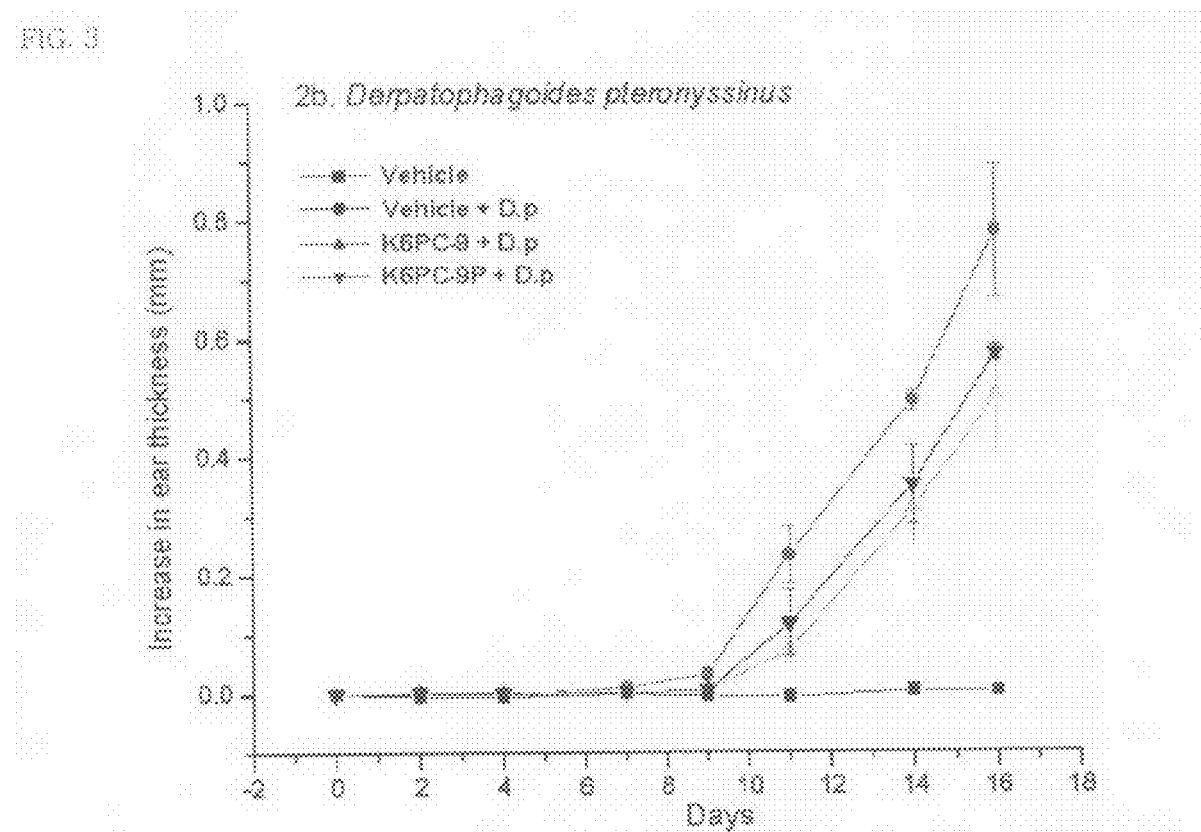
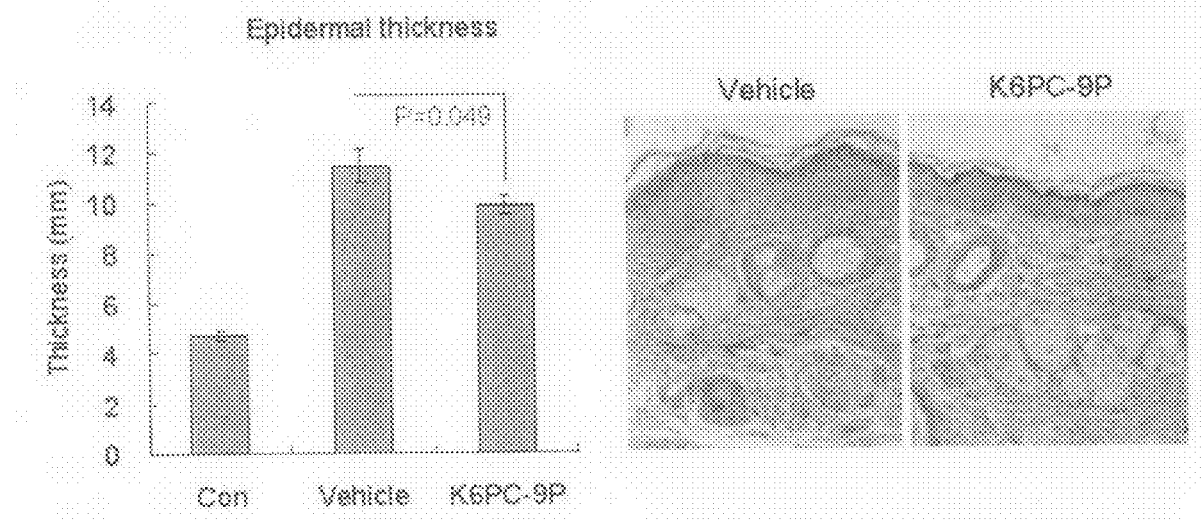

CERAMIDE DERIVATIVES, METHOD FOR PREPARING THE SAME, AND THERAPEUTIC AGENT FOR TREATING ATOPIC DERMATITIS COMPRISING THE CERAMIDE DERIVATIVES

TECHNICAL FIELD

The present invention relates to novel ceramide derivatives, a method for preparing the same, and a therapeutic agent for treating atopic dermatitis comprising the ceramide derivatives as active ingredients, and more particularly to novel ceramide derivatives, a method for preparing the same, and a therapeutic agent for treating atopic dermatitis capable of effectively treating atopic dermatitis by controlling ill-balanced immune functions of atopic dermatitis and suppressing or improving chronic inflammatory conditions, as well as suppressing hyperplasia which is one of skin disorders that are commonly observed in the atopic dermatitis.

BACKGROUND ART

Atopic dermatitis is one of incurable diseases and mainly divided into two paradigms, depending on their causes for the diseases. One is a inside-outside paradigm that atopic diseases are considered to be common allergic diseases and atopic dermatitis is caused by immunological disorders. The other is an outside-inside paradigm that a variety of allergic factors are easily penetrated into the skin owing to the dysfunction of skin barrier and therefore develop into the atopic dermatitis. According to the outside-inside paradigm, it is described that, since a barrier function against the skin penetration becomes weak with decreasing content of ceramide that is one main component in intercellular lipid of skin corneum, the skin develops into the atopic diseases due to the easy induction of xeroderma and the easy penetration of microorganism or allergens from outside environments. Accordingly, there has been an attempt to manage atopic diseases by supplementing lipid components such as ceramide in the corneum, or recovering its lamellar structure including the lipid components, and the present inventors have developed and merchandised analogous ceramide that is able to show an ability that is similar to the ceramide in vivo.

In addition to the barrier function recovery by the supplement of these ceramide formulations, it is, however, important to recover the damaged skin barrier functions (epidermal hyperplasia) and supplement barrier functions under the control of the differentiation of keratinocytes. In the case of the atopic dermatitis, the skin barrier functions are more seriously damaged by the epidermal proliferation, compared to the normal skin. Also, differentiation-associated proteins such as involucrin, loricrin, filaggrin and the like are expressed in a reduced amount or in abnormal patterns due to the deteriorated differentiation functions of the keratinocytes. Therefore, it is possible to improve atopic dermatitis through the improvement of the skin barrier functions using methods for suppressing epidermal proliferation caused by the barrier damages or facilitating normal differentiations of keratinocytes.

However, since it is difficult to treat atopic diseases by means of the recovery of the skin barrier function and the normal homeostasis of the skin, there has also been an attempt to develop a therapeutic agent for treating atopic dermatitis in aspect of its immunological pathogenesis. A variety of dermatitis including atopic dermatitis are referred to as inflammatory responses that are caused by the abnormal immune system in the skin, and therefore there have been various attempts to treat this dermatitis. Representative methods includes a method using a T cell inhibiting agent, a method using an anti-TNFα agent (malignant tumor necrosis factor-αagent), etc.

As a representative immunosuppressive agent, the T cell inhibiting agent includes calcineurin inhibiting agents such as cyclosporin, tacrolimus and pimecrolimus, and mycophenolate. The calcineurin inhibiting agents acts to suppress expression of interleukin-2(IL-2) and IL-2 receptor genes through the suppression of nuclear factor of activated T cells (NF-AT). Cyclosporin is not used as a topical agent since the cyclosporin shows a potent immunosuppressive effects when it is orally administered, but it does not penetrated into the skin when it is applied to the skin. On the contrary, tacrolimus and pimecrolimus have been approved for their use since they show a potent immunosuppressive effect when they are applied to the skin. However, when the tacrolimus and pimecrolimus are applied to the skin, they develop into various side effects such as the increase in infection rates due to the weakened immune system, as well as side effects such as burning, pruritus, erythema, irritation, edema, urticaria, etc. As another T cell inhibiting agent, the mycophenolate is an inhibiting agent of inhibiting purine biosynthesis in the de novo pathway that suppresses functions of T cells and B cells. It has been known that the mycophenolate is effective to treat atopic dermatitis when it is orally administered, but its effects have not been verified when it is applied to the skin.

TNFα is a proinflammatory cytokine that plays an important role in dermatitis. A representative anti-TNFα agent includes infliximab and etanercept. The infliximab and etanercept have been originally developed as a therapeutic agent for treating arthritis, and approved as the therapeutic agent for treating arthritis from FDA. In the clinical test, it has, however, been reported that the infliximab and etanercept are effective to treat various dermatitis including chronic dermatitis such as psoriasis, Behcet's syndrome, etc. It has been known that the infliximab and etanercept have various side effects in the digestive system and the respiratory system, as well as side effects such as headache. Also, the infliximab and etanercept are injected as antibody against the TNFα in protein formulations, but their effects are not proven when they are applied to the skin.

Although the above-mentioned immunosuppressive agents have various effects, they are used to treat severe dermatitis since they have their various side effects.

Accordingly, the therapeutic agents for treating atopic dermatitis, which do not have side effects and skin irritations and show their anti-inflammatory effects when they are applied to the skin, may be very useful as in the therapeutic agent for treating atopic dermatitis according to the present invention.

DISCLOSURE

Technical Problem

Accordingly, the present invention is designed to solve the problems of the prior art, and therefore it is an object of the present invention to provide novel ceramide derivatives.

It is another object of the present invention to provide a method for preparing the above-mentioned ceramide derivatives.

It is still another object of the present invention to provide a therapeutic agent for treating atopic dermatitis capable of effectively and safely treating atopic dermatitis by controlling ill-balanced immune functions of atopic dermatitis, suppressing or improving chronic inflammatory conditions, as well as suppressing hyperplasia which is one of skin disorders that are commonly observed in the atopic dermatitis, as well as of effectively treating epidermal proliferation such as psoriasis, eczema, contact dermatitis, etc. and various skin diseases such as inflammatory conditions in addition to the atopic dermatitis.

Technical Solution

In order to accomplish the above objects, the present invention provides novel ceramide derivatives represented by the following formula 1 or 2.

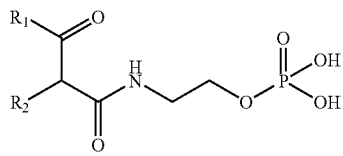

Formula 1 wherein, $R_1$ and $R_2$ are each independently straight or branched alkyl groups having 4 to 22 carbon atoms: and

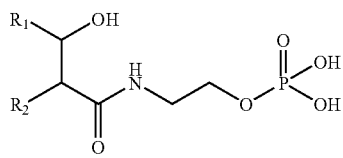

Formula 2 wherein, $R_1$ and $R_2$ are each independently straight or branched alkyl groups having 4 to 22 carbon atoms.

In order to accomplish the above objects, the present invention provides a method for preparing ceramide derivatives represented by the following formula 1 or 2 by phosphorylating a compound represented by the following formula 3 or 4:

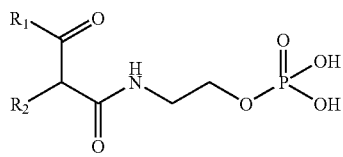

Formula 1 wherein, $R_1$ and $R_2$ are each independently straight or branched alkyl groups having 4 to 22 carbon atoms: and

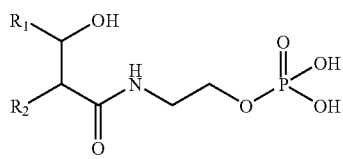

Formula 2 wherein, $R_1$ and $R_2$ are each independently straight or branched alkyl groups having 4 to 22 carbon atoms.

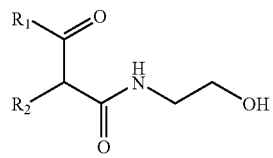

Formula 3

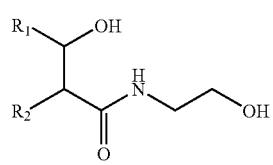

Formula 4

In order to accomplish the above objects, the present invention also provides a skin external composition comprising 0.001 to 50.0% by weight of the ceramide derivatives as defined in claim 1, based on the total weight of the composition.

DESCRIPTION OF DRAWINGS

These and other features, aspects, and advantages of preferred embodiments of the present invention will be more fully described in the following detailed description, taken accompanying drawings.

FIG. 3 is a graph showing results for effects of a therapeutic agent for treating atopic dermatitis according to the present invention on the suppression of dermatitis caused by dust mites in an animal model (NC/Nga mouse) where a mouse suffers from the atopic dermatitis.

FIG. 4 is a graph and a histologic photograph showing results for effects of a therapeutic agent for treating atopic dermatitis according to the present invention on the suppression of epidermal proliferation in a hyperplasia evaluation model using a hairless mouse.

BEST MODE

Figure 1:
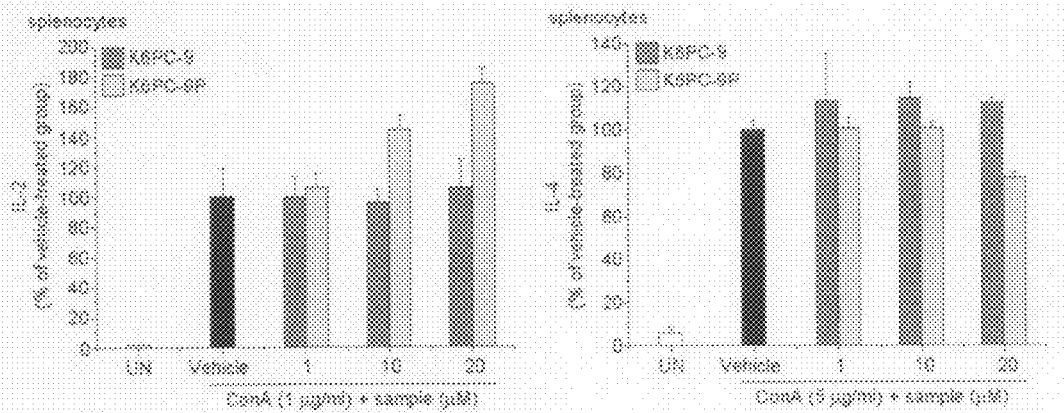
FIG. 1 is a graph showing results for an effect of a therapeutic agent for treating atopic dermatitis according to the present invention on generation of cytokines in T lymphocyte.

As a skin external agent, the therapeutic agent for treating atopic dermatitis according to the present invention may be useful to effectively treat atopic dermatitis by controlling ill-balanced immune functions of atopic dermatitis and suppressing or improving chronic inflammatory conditions, as well as suppressing or improving hyperplasia caused by the epidermal proliferation as the damaged skin barriers.

Also, the therapeutic agent for treating atopic dermatitis according to the present invention may be useful to effectively relieve or treat psoriasis, eczema, contact dermatitis and the like including epidermal proliferation and skin inflammatory conditions, as well as to treat atopic dermatitis.

The present inventors have firstly evaluated an effect of the therapeutic agent for treating atopic dermatitis on the generation of cytokines of helper T cells separated from a mouse, and then found that the atopic therapeutic agent may be useful to control ill-balanced immune functions of atopic dermatitis by increasing generation of interleukin-2 as Th1 cytokine and decreasing generation of interleukin-2 as Th1 cytokine, to effectively suppress dermatitis in the evaluation of the atopic dermatitis caused by dust mites in an animal model (NC/Nga mouse) where a mouse suffers from the atopic dermatitis, and to suppress epidermal proliferation in a hyperplasia evaluation model using a hairless mouse.

For the skin external composition according to the present invention, there is no particular limitation on the content of a therapeutic agent for treating atopic dermatitis as an active ingredient, but the atopic therapeutic agent is preferably present in a content of 0.001 to 50.0% by weight, more preferably in a content of 0.01 to 30.0% by weight, based on the total weight of the external composition. When the content of the atopic therapeutic agent is less than the above content range, effects of the therapeutic agent may be low, whereas the production cost may be high when the content of the atopic therapeutic agent exceeds the above content range.

Mode for Invention

Hereinafter, preferred embodiments of the present invention will be described in detail referring to the accompanying drawings. However, the description proposed herein is just a preferable example for the purpose of illustrations only, not intended to limit the scope of the invention, so it should be understood that other equivalents and modifications could be made thereto without departing from the spirit and scope of the invention.

SYNTHETIC EXAMPLE 1

Preparation of N-ethanol-2-hexyl-3-oxo-decanamide (K6PC-9)

500 ml of EtOH was added to 50 g (0.20 mol) of $C_6$ AKD (alkyl ketene dimer), and stirred thoroughly. 15 g (0.24 mol, 1.2 eq) of monoethanolamine was added to the resulting mixture, and stirred at a room temperature for 3 to 4 hours. 100 ml of 1N HCl was added to the resulting reaction solution, and the resulting mixture was extracted twice with 200 ml of methylene chloride. The methylene chloride phase was washed twice with 100 ml of saline. The methylene chloride phase was dried with $Na_2SO_4$, filtered, and then dried under a reduced pressured to remove solvents. The reaction mixture was separated using column chromatography (MC: EtOH=30:1), and dried under a reduced pressure to obtain 60 g (yield: 95%) of a white solid compound.

SYNTHETIC EXAMPLE 2

Preparation of N-(ethyl dihydrogenphosphate)-2-hexyl-3-oxo-decanamide (K6PC-9P)

150 ml of phosphorus oxychloride was added to 50 g (0.16 mol) of K6PC-9 prepared in Synthetic example 1, and stirred thoroughly for 48 hours. 100 ml of water was added to the resulting reaction solution, and the resulting mixture was extracted twice with 200 ml of ethyl acetate. The ethyl acetate phase was washed twice with 100 ml of saline. The ethyl acetate phase was dried with $Na_2SO_4$, filtered, and then dried under a reduced pressured to remove solvents. The reaction mixture was separated using column chromatography (EA: Hex=1:5), and dried under a reduced pressure to remove solvents, thereby to obtain 20 g (yield: 31%) of a white solid compound.

Rf (EA:Hex=1:5): 0.68

$^1$H NMR (400 MHz, $CDCl_3$): δ 0.87(t, 6H, $CH_3$), 1.21~1.40(br, 16H, $CH_2$), 1.56 (m, 2H, $CH_2CH_2CH_2CO$), 1.81(q, 2H, $CH_2CH_2CH(CO)CO$), 2.53 (t, 2H, $\overline{CH_2}CH_2CO$) 3.42 (t, 1H, $CH_2\overline{CH}(CO)CO$), 3.54(t, 2H, $NCH_2\overline{CH_2}OH$), 3.60(t, 2H, $NCH_2\underline{CH_2}OH$), 6.75 (br, 1H, NH)

K6PC-9
$C_{18}H_{35}NO_3$
Mol. Wt.: 313.48

K6PC-9P
$C_{18}H_{36}NO_6P$
Mol. Wt.: 393.46

Hereinafter, effects of the previously prepared compounds were evaluated in Examples and Comparative example. First, the Examples were carried out using N-(ethyl dihydrogenphosphate)-2-hexyl-3-oxo-decanamide (hereinafter, referred to as 'K6PC-9P') wherein $R_1$ and $R_2$ are $C_6$ in the above-mentioned formulas 1 and 2, and the Comparative example was carried out using N-ethanol-2-hexyl-3-oxo-decanamide (hereinafter, referred to as 'K6PC-9') in an unphosphorylated form of the K6PC-9P from the Examples.

EXAMPLE 1

Effects on Generation of Cytokines in T Lymphocyte

First, in order to determine effects of K6PC-9P and K6PC-9 on generation of cytokines in T lymphocyte, spleen T lymphocyte was separated, and then treated with ConA for its activation. The activated spleen T lymphocyte shows ill-balanced immune responses of helper T cells in the atopic dermatitis, wherein the Th1 cytokines such as, interleukin-2, 12, etc. were expressed in a decreased amount, and the Th2 cytokine such as interleukin-4, 5, 6, 10, 13, etc. were expressed in an increased amount. Accordingly, substances that increase the expression of the Th1 cytokines or suppress the expression of the Th2 cytokines may be useful to treat the atopic dermatitis. In this experiment, the K6PC-9P and K6PC-9 were evaluated for their control abilities to express the Th1 cytokine, interleukin-2, and the Th2 cytokine, interleukin-4.

The mouse spleen was extracted from a Balb/C mouse to separate splenocyte. The separated splenocyte was plated onto a 96-well plate in a density of $1 \times 10^6$ cells/ml. Then, T lymphocyte in the splenocyte was activated with ConA (1 μg/ml). The K6PC-9P and K6PC-9were pre-treated 30 minutes before the treatment with ConA. 48 hours after the treatment with ConA, culture supernatant was collected, and subject to the ELISA (enzyme-linked immunosorbent assay). The ELISA used an ELISA kit from a R&D system, and performed experiments, as follows. However, the method specified later is described as one example, and the method is identical over the entire procedures, but densities of antibodies and standard sample may be slightly varied depending on the kinds of cytokines to be measured. A capture antibody was diluted to a density of 0.6 µg/ml, and transferred to an ELISA plate by 100 µl, and the plate was sealed and kept overnight at a room temperature. The capture antibody was discarded, and the plate was washed three times with a wash buffer (PBS containing 0.05% Tween 20 (pH 7.4)). 200 µl of a blocking buffer (PBS containing 1% BSA, 5% sucrose and 0.05% NaN) was put into plate wells, kept at a room temperature for 1 hour, and then washed three times with a wash buffer. The collected culture supernatant and the standard sample were prepared using a dilution buffer (TBS containing 0.1% BSA and 0.05% Tween 20), put into plate wells, and then kept at a room temperature for 2 hours. The plate was washed three times with a wash buffer, and a biotinylated detection antibody was diluted with a dilution buffer to a density of 200 ng/ml, and then put into the plate wells. 2 hours after the treatment, the plate was washed three times with a wash buffer, and streptavidin HRP was added to the plate, and then kept for 20minutes. The plate was washed three times with a wash buffer, and a substrate solution was added to the plate to develop colors. When the colors were suitably developed on the plate, the reaction was stopped with a stop solution (1M $H_2SO_4$), and its absorbance was measured at wavelengths of 450 nm and 540 nm. A standard curve was plotted using the standard absorbance obtained by subtracting a 540 nm absorbance value from a 450 nm absorbance value, and a density of cytokines to be measured was calculated using the standard absorbance of the culture supernatant.

When the mouse spleen cells were treated with the K6PC-9P and K6PC-9 in density of 1, and 20 µM, respectively, it was revealed that the K6PC-9P of Example 1 increases the generation of the Th1 cytokine, interleukin-2, and decreases the generation of the Th2 cytokine, interleukin-4, as shown in FIG. 1, but it was confirmed that the K6PC-9 of the comparative example does not affect the generation of IL-2 and IL-4 by the treatment with ConA. This result indicates that the therapeutic agent for treating atopic dermatitis according to the present invention is very effective to control ill-balanced immune functions in the atopic dermatitis to treat the atopic dermatitis.

EXAMPLE 2

Efficiency Evaluation Using Animal Model (NC/Nga Mouse) where Mouse Suffers from Atopic Dermatitis Next, an animal model (NC/Nga mouse) where a mouse suffers from atopic dermatitis was used to evaluate an inflammation control effects of the K6PC-9P on the atopic dermatitis. The NC/Nga mouse is a mouse that spontaneously suffers from the dermatitis, and has been proven to be an animal model that is the most suitably used to treat atopic dermatitis. Therefore, The NC/Nga mouse has been widely used in the animal model to evaluate substances that are effective to treat the atopic dermatitis. For this experiment, a dust mite that is a representative inducer factor of the atopic dermatitis was applied to a NC/Nga mouse to induce the dermatitis.

The extract of dust mite (*Dermatophagoides pteronyssinus*, *Dermatophagoides farinae*) was commercially available from Woongbee Meditech Co. (Korea), and the dust mite extract was dissolved in 10 mg/ml of phosphate buffered saline (PBS) containing 0.5% Tween 20, and then used herein. NC/Nga mice were bred under conventional breeding conditions, and induced to develop into the atopic dermatitis. And, the dust mite extract was applied onto ear dorsal surfaces of the mice three times per week, and this experiment was carried out for 16 days. The K6PC-P and K6PC-9 were applied onto the ear dorsal surfaces of the mice 30 minutes before the application of the dust mite extract, and the efficiency of the therapeutic agent was evaluated for a level of an intercurrent disease by measuring a thickness of a mouse ear.

Figure 2:
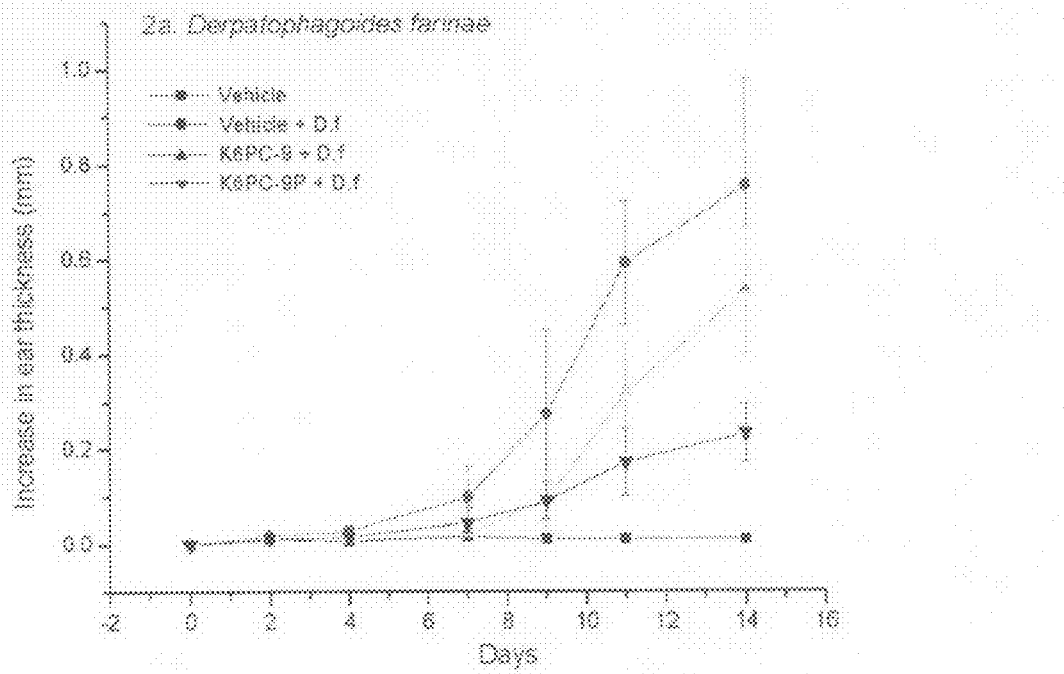
FIG. 2 is a graph showing results for effects of a therapeutic agent for treating atopic dermatitis according to the present invention on the suppression of dermatitis caused by dust mites in an animal model (NC/Nga mouse) where a mouse suffers from the atopic dermatitis.

As a result, it was confirmed that the K6PC-9P significantly suppresses the increase in the thickness of the mouse ear since it relieves the atopic dermatitis symptoms caused by two kinds of dust mites in the case of Examples, as shown in FIGS. 2 and 3. On the contrary, it was seen that the K6PC-9 suppresses the increase in the thickness of the mouse ear caused by the dust mite extract, but the K6PC-9 has a slight suppression effect when compared to that of the K6PC-9P in the case of the comparative example. This result indicates that the therapeutic agent for treating atopic dermatitis according to the present invention may be used to effectively treat skin inflammations in the atopic dermatitis in addition to the immunoregulatory functions as described in Example 1.

EXAMPLE 3

Effects on Suppression of Epidermal Proliferation

Next, in order to evaluate effects of the K6PC-9P on the skin hyperplasia that is one of the representative skin disorders in the atopic dermatitis, a hyperplasia model where a mouse has overgrown cuticles was established by repeating a tape stripping procedure on a hairless mouse in the Examples according to the present invention. This hyperplasia model was established since the atopic skin has ill-balanced conditions in the epidermal proliferation and differentiation, and particularly has an increased epidermal proliferation level, but has a pattern in which mouse epidermis grows abnormally due to the reduced differentiation level. Accordingly, to recover this ill-balanced condition into a normal state may be considered to be an important point to treat the atopic dermatitis.

Hyperplasia in the back of a hairless mouse was induced by subjecting the tape stripping procedure twice per day for 5 days, and 1% K6PC-9P was applied to the hairless mouse twice per day for 3 days from the third day to fifth day of the induction of the atopic dermatitis. Then, mouse skin tissues were biopsied and fixed into a paraffin wax, and determined for epidermal thickness using a Hematoxylin & Eosin staining method. As a result, when the K6PC-9P was applied to the mouse as shown in FIG. 1, it was observed that the growth of the mouse epidermis is suppressed significantly, compared to the control (vehicle). Therefore, it was proven that the K6PC-9P functions to treat skin hyperplasia conditions that are representative skin barrier abnormalities in the atopic dermatitis. The overgrowth of the mouse epidermis causes the abnormally grown skin corneum, which leads to the coarse and thick skins, and therefore possibilities to cause various problems regarding xeroderma atopic dermatitis, psoriasis and the like may be increased since the abnormal differentiation prevents normal skin barrier functions.

FORMULATION EXAMPLE 1

Treatment with Emollient Cream

A humectant was added to purified water, and heated to a temperature of 70° C. The K6PC-9P and an oily component were dissolved by heating. Then, an emulsifying agent and a preservative were added to the resulting mixture, and heated to a temperature of 70° C. The resulting mixture solution was added to the previously prepared aqueous phase, and emulsified particles were homogenized in a Homo mixer, deformed, filtered and cooled.

TABLE 1

| Functions | Components | Content (%) |
|---|---|---|
| Main compoent | K6PC-9P | 1.0 |
| Oily component | Cetostearyl alcohol | 6.0 |
| | Stearic acid | 2.0 |
| | Lanolin | 4.0 |
| | Squalane | 9.0 |
| | Octyldodecanol | 10.0 |
| Humectant | 1,3-Butylene glycol | 3.0 |
| | Glycerine | 2.0 |
| Emulsifying agent | POE(25) Cetyl alcohol ether | 3.0 |
| | Glyceryl monostearate | 2.0 |
| Preservative | Propyl paraben | Suitable amount |
| | Methyl paraben | Suitable amount |
| | Purified water | the Balance |

FORMULATION EXAMPLE 2

Treatment with External Ointment

The K6PC-9P and an oily component were dissolved by heating. Then, an emulsifying agent and a preservative were added to the resulting mixture, and heated to a temperature of 70° C. The resulting mixture solution was homogenized in a Homo mixer, deformed, filtered and cooled.

TABLE 2

| Functions | Components | Content (%) |
|---|---|---|
| Main compoent | K6PC-9P | 1.0 |
| Oily component | Petrolatum | the Balance |
| | Cetostearyl alcohol | 2.0 |
| | Lanolin | 3.0 |
| | Squalane | 3.0 |
| Emulsifying agent | Ceteareth-20 | 3.0 |
| Preservative | Propyl paraben | Suitable amount |
| | Methyl paraben | Suitable amount |

FORMULATION EXAMPLE 3

Treatment with Humectant Lotion

A humectant was added to purified water, and heated to a temperature of 70° C. The K6PC-5 and an oily component were dissolved by heating. Then, an emulsifying agent and a preservative were added to the resulting mixture, and heated to a temperature of 70° C. The resulting mixture solution was added to the previously prepared aqueous phase, and homogenized in a Homo mixer, deformed, filtered and cooled.

TABLE 3

| Functions | Components | Content (%) |
|---|---|---|
| Main compoent | K6PC-9P | 1.0 |
| Oily component | Cetostearyl alcohol | 1.0 |
| | Wax | 0.5 |
| | Vassline | 2.0 |
| | Squalane | 6.0 |
| | dimethyl siloxane | 2.0 |

TABLE 3-continued

| Functions | Components | Content (%) |
|---|---|---|
| Emulsifying agent | POE(10) Monooleate ester | 1.0 |
| | Glycerol monooleate ester | 1.0 |
| Preservative | Glycerin | 4.0 |
| | 1,3-Butylene glycol | 4.0 |
| Humectant | Propyl paraben | Suitable amount |
| | Methyl paraben | Suitable amount |
| Others | 1% Aqueous hyaluronic acid solution | 3.0 |
| | Purified water | the Balance |

INDUSTRIAL APPLICABILITY

The ceramide derivatives according to the present invention and the therapeutic agent for treating atopic dermatitis may be useful to control ill-balanced immune functions of atopic dermatitis by increasing generation of interleukin-2 as Th1 cytokine and decreasing generation of interleukin-2 as Th1 cytokine through the evaluation for the effects of the therapeutic agent for treating atopic dermatitis on the generation of cytokines in helper T cells separated from a mouse, to effectively treat various skin diseases such as epidermal proliferations or inflammatory conditions, for example psoriasis, eczema, contact dermatitis and the like as well as the atopic dermatitis by effectively suppressing dermatitis in the evaluation of the atopic dermatitis caused by dust mites in an animal model (NC/Nga mouse) where a mouse suffers from the atopic dermatitis, and suppressing epidermal proliferation in a hyperplasia evaluation model using a hairless mouse.

The invention claimed is:

1. Ceramide derivatives represented by the following formula 1 or 2:

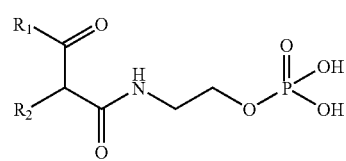

Formula 1 wherein, $R_1$ and $R_2$ are each independently straight or branched alkyl groups having 4 to 22 carbon atoms: and

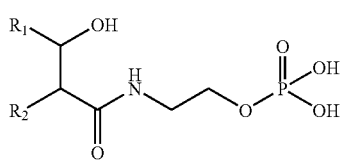

[formula 2]

wherein, $R_1$ and $R_2$ are each independently straight or branched alkyl groups having 4 to 22 carbon atoms.

2. The ceramide derivatives according to claim 1, wherein the $R_1$ and $R_2$ are $C_6$.

3. The ceramide derivatives according to claim 1, wherein the ceramide derivatives represented by the formula 1 or 2 are N-(ethyl dihydrogenphosphate)-2-hexyl-3-oxo-decanamide, or N-(ethyl dihydrogenphosphate)-2-hexyl-3-hydroxy-decanamide.

4. The ceramide derivatives according to claim 2, wherein the ceramide derivatives represented by the formula 1 or 2 are N-(ethyl dihydrogenphosphate)-2-hexyl-3-oxo-decanamide, or N-(ethyl dihydrogenphosphate)-2-hexyl-3-hydroxy-decanamide.

5. A skin external composition comprising 0.001 to 50.0% by weight of the ceramide derivatives as defined in claim 1, based on the total weight of the composition.

* * * * *